United States Patent
Kim

(10) Patent No.: US 9,565,829 B2
(45) Date of Patent: Feb. 14, 2017

(54) **STRAIN OF *LENTINULA EDODES* GNA01**

(75) Inventor: Young Chan Kim, Gyeongsangnam-do (KR)

(73) Assignee: Young Chan Kim, Gyeongsangnam-do (KR)

( * ) Notice: Subject to any disclaimer, the term of this patent is extended or adjusted under 35 U.S.C. 154(b) by 669 days.

(21) Appl. No.: 13/994,696

(22) PCT Filed: Dec. 2, 2011

(86) PCT No.: PCT/KR2011/009330
§ 371 (c)(1),
(2), (4) Date: Jun. 14, 2013

(87) PCT Pub. No.: WO2012/081851
PCT Pub. Date: Jun. 21, 2012

(65) Prior Publication Data
US 2013/0291225 A1    Oct. 31, 2013

(30) Foreign Application Priority Data
Dec. 16, 2010 (KR) .................. 10-2010-0128902

(51) Int. Cl.
*A01H 15/00* (2006.01)
*C12R 1/645* (2006.01)
(52) U.S. Cl.
CPC ............... *A01H 15/00* (2013.01); *C12R 1/645* (2013.01)

(58) Field of Classification Search
USPC ........................................... Plt./394
See application file for complete search history.

(56) References Cited

FOREIGN PATENT DOCUMENTS

| | | |
|---|---|---|
| JP | 08-149934 A | 6/1996 |
| JP | 2002-238350 A | 8/2002 |
| JP | 2002-253073 A | 9/2002 |
| KR | 10-0703050 B1 | 4/2007 |

OTHER PUBLICATIONS

Korean National Seed & Variety Service, Jun. 15, 2010, Variety Protection Publication No. 143, p. 356, Registration No. 11-1380961-000003-08 (Translation provided by Applicant).*
Korean Seed & Variety Service, FAQ Plant Variety Protection downloaded from seed.go.kr/english/function/system.jsp on Jun. 7, 2016.*
International Search Report for PCT/KR2011/009330.
Variety Protection Publication No. 143 (Registration No. 11-1380961-000003-08, Korea Seed & Variety Service) Jun. 15, 2010 (See p. 356. The English translation of p. 356 is submitted herewith.).

* cited by examiner

*Primary Examiner* — David H Kruse
(74) *Attorney, Agent, or Firm* — The PL Law Group, PLLC

(57) ABSTRACT

Disclosed is a novel shiitake strain *Lentinula edodes* (Berk.) Pegler GNA01 (accession No: KCCM11135P) and a fruit body produced by culturing the same. The fruit body exhibits a new morphology and a new taste.

8 Claims, 2 Drawing Sheets

STRAIN OF *LENTINULA EDODES* GNA01

CROSS REFERENCE TO RELATED APPLICATIONS AND CLAIM OF PRIORITY

This patent application is a National Phase application under 35 U.S.C. §371 of International Application No. PCT/KR2011009330, filed Dec. 2, 2011, which claims priority to Korean Patent Application No. 10-2010-0128902 filed Dec. 16, 2010, entire contents of which are incorporated herein by reference.

BACKGROUND

1. Technical Field

The present invention relates to a *Lentinula edodes* strain. More particularly, the present invention relates to a novel strain of shiitake mushrooms [*Lentinula edodes* (Berk.) Pegler] with new morphology and taste, identified as *Lentinula edodes* GNA01 (Accession No.: KCCM11135P), and a fruit body obtained by culturing the stain.

2. Description of the Related Art

Shiitake mushrooms (also called as pyogo, binomial name: *Lentinula edodes* (Berk.) Pegler), belonging to the *Lentinula* genus of the Marasmiaceae family, were first introduced into the academic world by the English botanist Berkeley after he collected them in Japan. Shiitake mushrooms are native to Korea, China, and Japan. In Korea, shiitake mushrooms are given various names, for example, hyangsim, mago, and oak tree mushroom, and are known as a member of the three famous edible mushrooms inclusive of pine mushrooms and *Sarcodon aspratus*.

Shiitake mushrooms bud and grow on dead bodies or branches of broadleaf trees such as oak trees (e.g., acorn trees, Mongolian oak, Korean oak), red-Leaved Hornbeam, chestnut trees, etc., from the spring to the fall, but can now be artificially cultivated. Unlike other mushrooms, shiitake mushrooms are grown at moderate temperatures (optimal 22~28° C., up to 32° C.).

Shiitake mushrooms generally produce extensive mycelia with clamp connections. This fungal species is dioecious with tetrapolarity. When the spores of the mushrooms germinate, they produce hyphae, called monokaryons, with a single nucleus in each compartment. At some stage in their growth, two monokaryons of different compatibility groups fuse to form a dikaryon (hybrid strain). The dikaryon is brown-colored and hardens under light, developing into a fruit body. The hyphal growth of shiitake mushrooms, although slower than that of oyster mushrooms, occurs well in oak tree logs.

The fruit body, as shown in FIGS. 1 and 2, is hemiangiocarpous and has a stipe connected to the center of a pileus from which lamellae spread. The pileus is pale or dark brown, while both the stipe and the lamellae are white. The pileus is round with a various diameter range including less than to 3 cm and greater than 10 cm, depending on nutrients, environment and species. The pileus curls inward in the early stage of the fruit body development, but becomes flatter as the fruit body grows larger. Shiitake mushrooms have a hard fleshy body, and its characteristic scent is stronger when it is dried. The lamellae are thin and white and the stipe is white or brownish while being toughly fibrous.

In the 1970s, lentinan, a β-D-glucan derived from shiitake mushrooms, was found to have anticancer activity. Since then, pharmaceutical activity of shiitake mushroom has been studied (Chihara et al., 1970; Tamura et al., 1997). Among nutrients found in shiitake mushrooms are crude proteins, glycolipids, ash, carbohydrates, fiber, and amino acids. In recent years, shiitake mushrooms have been processed into various foods, snacks, fermented milk drinks, soups, etc. (Ryu, 1998), and actively studied for physiologically active ingredients having anti-inflammation, anti-hypertension, and antithrombosis effects (Ohnuma et al., 2000, Yaoita et al., 1998, 1999).

However, shiitake mushrooms, unlike other mushrooms, have a single crop period of as long as 4~5 years, and high expense is required for studies on of the breeding of shiitake mushrooms. Under these circumstances, studies for developing variants of shiitake mushrooms have mainly been undertaken by the Forest Mushroom Research Center under the support of the National Forestry Cooperative Federation, and by the Korea Forest Research Institute in Korea.

Only an extremely limited number of Korean variants of shiitake mushroom have been bred, and none of them are better in general properties than Japanese variants. There is a need for new variants of shiitake mushrooms. Because the International Convention for the Protection of New Varieties of Plants according to the Union Internationale Pour la Protection des Obtentions Vegetales (UPOV) has been applied to shitake mushroom since 2008, a royalty must be paid on the use of Japanese or Chinese variants.

Therefore, there is a pressing need for developing a novel variant of shiitake mushrooms that is superior to conventional variants including Japanese and Chinese mushrooms in terms of general properties.

SUMMARY

With in mind the above problems occurring in the prior art, the present inventors conducted research into the development of a novel shiitake mushroom strain, which results in the present invention.

It is an object of the present invention to provide a novel variant of shiitake mushrooms which are generally similar to a spherical shape with both the stipe and the pileus integrated into a globe or sphere-like shape.

It is another object of the present invention to provide a novel variant of shiitake mushroom which not only has a scent characteristic of shiitake mushroom, but also has a sweet taste.

It is another object of the present invention to provide a novel variant of shiitake mushroonms which have a harder flesh than conventional shiitake mushrooms, and that can be stored for a period of two or more times longer and outgrow by two or more times the conventional shiitake mushrooms, without the opening of the pileus.

It is a further object of the present invention to provide a novel variant of shiitake mushrooms which exhibit a white blooming appearance on the surface of the fruit body and thus is superior to conventional shitake mushroom in terms of commercial value.

It is a still further object of the present invention to provide a novel variant of shiitake mushrooms which are resistant to weather, particularly to high and low temperatures, and thus can be produced throughout the year.

The above and other objects, features and other advantages of the present invention will be more clearly understood from the following detailed description.

The above objects could be accomplished by a provision of a novel shiitake mushroom strain *Lentinua edodes* (Berk.) Pegler GNA01. This strain was deposited with the Korean Culture Center of Microorganisms on Nov. 23, 2010 (accession No.: KCCM11135P).

In addition, the present invention provides a fruit body of shiitake mushrooms grown from the strain of claim 1.

In one preferred embodiment, the fruit body is similar to a spherical shape with no discrimination between a pileus and a stipe.

In another preferred embodiment, the fruit body tastes sweet.

In a further preferred embodiment, the fruit body exhibits a white blooming appearance on its surface.

In a still further preferred embodiment, the fruit body is asporogenous.

In still another preferred embodiment, the novel strain is proliferated through tissue dissociation of a part of the fruit body.

Features of the novel strain of shiitake mushrooms according to the present invention are as follows.

First, the shiitake mushroom of the present invention has no distinct pilei and stipes, but is generally similar to a spherical shape, with both the pileus and the stipe integrating into a globe or sphere-like shape.

Unlike conventional shiitake mushrooms with characteristic scent, the novel shiitake mushroom strain of the present invention tastes sweet as well as having a characteristic scent.

In addition, the novel shitake mushroom strain of the present invention has harder flesh than conventional shiitake mushrooms, and can be stored for a period of two or more times longer and outgrow by two or more times conventional shiitake mushrooms, without the opening of the pileus.

Further, the novel shiitake mushroom strain of the present invention exhibits a white blooming appearance on the surface of the fruit body, and thus is superior to conventional shitake mushrooms in terms of commercial value.

Moreover, the novel shiitake mushroom strain of the present invention is resistant to weather, particularly to high and low temperatures, and thus can be produced throughout the year.

DETAILED DESCRIPTION

Figure 1:
FIG. 1 is a photograph of conventional shiitake mushrooms which are under growth.
Figure 2:
FIG. 2 is a photograph showing the general morphology of the conventional shiitake mushroom of FIG. 1 after harvest, and a longitudinal cross-section thereof.
Figure 3:
FIG. 3 is a photograph of the novel shiitake mushroom strain of the present invention (*Lentinua edodes* (Berk.) Pegler} GNA01) which is under growth.
Figure 4:
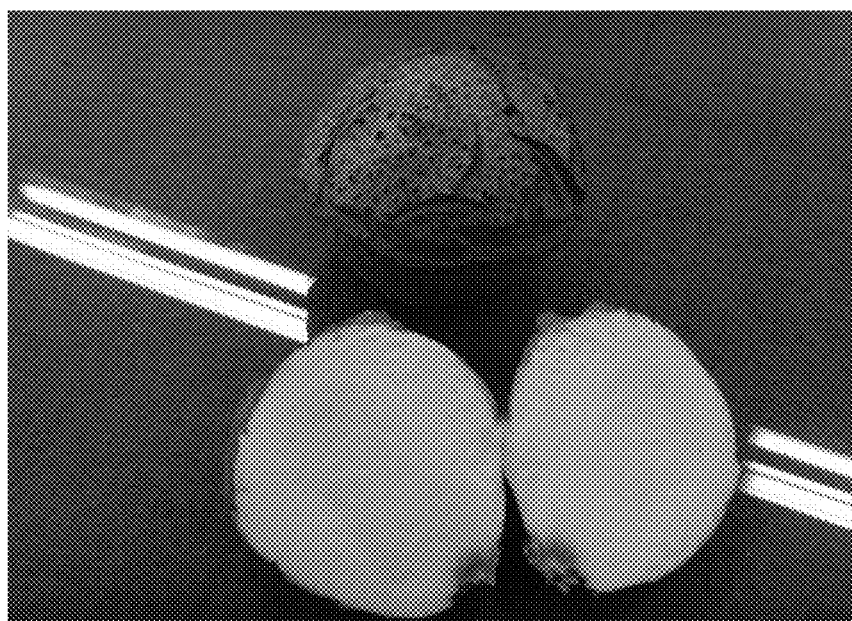
FIG. 4 is a photograph showing the general morphology of the novel shiitake strain *Lentinula edodes* (Berk.) Pegler GNA01 of FIG. 3 after harvest, and a cross-section thereof

To explain the present invention well and to instruct those skilled in the art to perform the present invention, as many general terms which are widely spread in the art as possible are employed. The terms that the present inventors inevitably select for the delineation of specific points should not be construed as simply the meanings of the words themselves, but in the context of the phrases or sentences in which they are employed.

Reference should now be made to the drawings and preferred embodiments to elucidate the present invention.

However, the present invention is not limited to the embodiments given herein, and may be embodied into another modality. Throughout the specification, the same reference numerals are used to designate the same or similar components.

In accordance with an aspect thereof the present invention addresses a novel shiitake mushroom strain *Lentinula edodes* (Berk.) Pegler GNA01 capable of produce a fruit body which is similar to a spherical shape in morphology with no distinct stipes and pilei.

The novel shiitake mushroom strain *Lentinula edodes* (Berk.) Pegler GNA01 (accession No: KCCM11135P) according to the present invention can produce a fruit body which looks like a globe or sphere-like shape with neither pileus nor spite differentiation.

All of the shiitake mushrooms known thus far have pilei and stipes irrespective of their variants. In contrast, the novel strain *Lentinula edodes* (Berk.) Pegler GNA01 according to the present invention forms a globe or sphere-like shape in which neither pilei nor stipes are distinct. The spherical fruit body is superior to conventional shiitake mushroom in terms of sensation of eating as well as taste and flavor. Particularly, the novel shiitake mushroom strain tastes sweet in addition to having a characteristic scent. Moreover, the novel shiitake mushroom strain exhibits a white blooming appearance on the surface of the fruit body, and is thus commercially more valuable.

The novel strain according to the present invention was developed by crossing monokaryotic shiitake strains. As will be stated in detail, two monokaryotic strains are crossed with each other to form a primary hybrid stain which is then backcrossed with one monokaryotic mother strain to give a secondary hybrid strain. The primary and the secondary hybrid strains are again crossed to afford the novel strain of the present invention. Because there are no established phylogenetic relationships among shiitake mushrooms, it is impossible to determine the phylogenetic position of the novel strain. However, when morphological, physiological and cultural properties are taken into consideration, the novel strain obtained by hybridizing monokaryotic strains of shiitake mushrooms is identified as *Lendinula edodes* (Berk.) Pegler GNA01. A description will be given of the morphological, physiological and cultural properties of the novel strain below.

EXAMPLE 1

Isolation and Morphological Properties of Novel Shiitake Mushroom Strain

1. Formation of $1^{st}$ Generation Hybrid Strain

Sammyungjin Research Institute L26, located in Fujian Province, China, and Kyoungwon 9015(939) were used as mother strains for the development of the novel strain of the present invention.

(1) Isolation of Single Spores

Pilei of the shiitake mushroom strains L26 and Kyoungwon 9015(939) were placed on respective Petri dishes, and after 24 hrs, spores fallen on the Petri dishes were collected, diluted to a suitable concentration in sterile water, and spread over potato agar plates. Primary hyphae germinated by culturing the spores at 25° C. were separated using toothpicks, followed by inoculating the hyphae into respective potato agar plates. These potato agar plates were incubated at 25° C. for 14 days, after which hyphae were separated from the plates and observed for the formation of clamp connection under a microscope. Only the hyphae without clamp connection were stored in a 10% glycerol solution and kept in the fridge until use in experiments.

(2) Hybridization

Purely separated single spores of shiitake mushroom (monokaryotic) were inoculated into potato agar plates, and incubated at 25° C. for 14 days. For use in hybridization, the hyphae which grew well and were abundant in mycelium quantity were selected. The selected monokaryotic mycelia, that is, the mycelia grown on the potato agar plates, were cut into a circular shape with a diameter of 1 cm. One single hypha (monokaryotic) and another single hypha (monokaryotic) were inoculated 3 cm apart from each other into a fresh potato agar plate which was then incubated at 25° C. for 15~20 days in an incubator. Hyphae were separated and observed by microscopy to determine the formation of clamps. A selection was made of the stains in which clamps were formed.

(3) Cultivation of $1^{st}$ Generation Hybrid Strain

Oak sawdust, white birch sawdust, and wheat bran were mixed at a ratio of 3:1:1, and the mixture was allowed to have a water content of 62%. An 850 cc bottle for culturing mushrooms was charged with 580 g of the mixture. A rod with a diameter of 2 cm was pushed at the center of the entry of the bottle from the top to the bottom to form a pathway extending through the mixture, followed by sterilizing at 105° C. for 70 min under atmospheric pressure and then autoclaving at 121° C. for 110 min under a high pressure. After the bottle was cooled to 17° C., the selected strains were inoculated and cultured at 22° C. for 50 days in a dark condition. The medium was transferred into a browning chamber and perforated once or more times to adjust the water content After completion of browning for 60 days, the medium was moved into a breeding chamber, immersed in water, and subjected to germination and cultivation at 17~23° C. with humidity of 85%-90%.

2. Formation of $2^{nd}$ Generation Hybrid Strain (1) Isolation of Monokaryotic Hyphae Single spores were isolated from the fruit body of the cultured $1^{st}$ generation hybrid strain and treated in the same manner as described above to produce monokaryotic hyphae which were then stored in the fridge until use in experiments.

(2) Hybridization

The purely isolated monokaryotic hyphae of L26 and the monokaryotic hyphae of the $1^{st}$ generation hybrid strain were crossed in the same manner as is described above to select a $2^{nd}$ hybrid strain.

(3) Cultivation of $2^{nd}$ Generation Strain

The $2^{nd}$ generation hybrid strain was cultured in the same manner as is described for the $1^{st}$ generation strain.

3. Formation of Novel Strain *Lentinula edodes* (Berk.) Pegler GNA01

(1) Isolation of Monokaryotic Hyphae

Single spores were isolated from the fruit body of the cultured $2^{nd}$ generation hybrid strain and treated in the same manner as described above to produce monokaryotic hyphae which were then stored in the fridge until use in experiments.

(2) Hybridization

The purely isolated monokaryotic hyphae of the $1^{st}$ and the $2^{nd}$ hybrid strains were crossed in the same manner as is described above to select a strain with clamp connection, which was to be identified as *Lentinua edodes* (Berk.) Pegler GNA01.

(3) Cultivation of *Lentinula edodes* (Berk.) Pegler GNA01

*Lentinula edodes* (Berk.) Pegler GNA01 was cultured in the same manner as is described for the $1^{st}$ generation strain.

4. Selection of Novel Shiitake Mushroom Strain

Among the fruit bodies bred, primary selection was made of those which were excellent in terms of morphology, color and polish, size, and taste. Then, a fruit body which was almost completely spherical in morphology, dense, but not too hard in tissue, and exhibited a white blooming appearance throughout its surface, was selected again.

The novel strain, *Lentinula edodes* (Berk.) Pegler GNA01, was duly deposited with Korean Culture Center of Microorganisms (having the address of KCCM, 3F Yurim B/D, 361-221, Hongje-1-dong, Sudaemun-gu, Seoul 120-091, Republic of Korea) under the Access number of KCCM11135P on Nov. 23, 2010. The deposit has been made under the terms of the Budapest Treaty and all restrictions imposed by the depositor on the availability to the public of the biological material will be irrevocably removed upon the granting of a patent.

5. Morphological Features of *Lentimda edodes* (Berk.) Pegler GNA01

*Lentinula edodes* (Berk.) Pegler GNA01 looks like one spherical globe with neither piles nor spites formed therein. Because the novel strain has neither pilei nor spites, it does not exhibit the opening of pileus. It grows twice as large as typical shiitake mushrooms, with a weight amounting up to 150 g. The tissue of *Lentinula edodes* (Berk.) Pegler GNA01 is soft, elastic and white, and tastes sweet with a characteristic flavor. The sensation of eating is very good because it is chewy. The flesh of *Lentinula edodes* (Berk.) Pegler GNA01 is harder than that of conventional shiitake mushrooms, and exhibits a white blooming appearance throughout its surface, which improves the commercial value of the fruit body of Lentimda *edodes* (Berk.) Pegler GNA01. Because *Lentinula edodes* (Berk.) Pegler GNA01 is asporogenous, its propagation is conducted by tissue dissociation of the fruit body thereof.

EXAMPLE 2

Physiological Properties of *Lentimda edodes* (Berk.) Pegler GNA01

(1) Optimal Temperature for Hyphal Growth:

The mycelia grown on potato agar plates were cut into a size with a diameter of 10 mm, inoculated into a center of respective MCM agar plates, and cultured at various temperatures for 14 days. Measurements of the grown mycelia indicated a growth temperature ranging from 5° C. to 29° C., with an optimum temperature of 17-23° C. for a daylight condition and 5-10° C. for a night condition.

(2) Optimal Acidity for Hyphal Growth:

To investigate optimal activity for hyphal growth, 25 mL of glucose peptone-yeast extract broth was adjusted in pH of from 4 to 8. After stationary culturing for 14 days, dried mycelia were weighed, indicating that acidity available for hyphal growth ranges from 4.5 to 8, with an optimal pH of approximately 6.5.

EXAMPLE 3

Cultivation of Novel Strain *Lentinula edodes* (Berk.) Pegler GNA01

1. Preparation of Medium
(1) Raw Materials
① Broadleaf Tree Sawdust (Oak Tree)
Broadleaf tree sawdust available for culturing *Lendinula edodes* (Berk.) Pegler GNA01 is 5 mm or less in chip size, with a fresh and vivid color. The sawdust has a water content of 14~18%, and exhibits pH of around 8.0 with a total nitrogen content of 0.3% or greater. Cadmium content is strictly limited to the standard or less. Acorn with an age of 12 to 15 years is preferred. Preferably, it ranges in diameter from 12 to 15 cm. The sawdust is preferably composed of 60% chips with a size of 3~5 mm, 30% chips with a size of 2~3 mm, and 10% chips with a size of 1~2 mm.

② White Birch Sawdust

A medium for culturing shiitake mushroom generally contains sugar as an organic carbon source. Instead of sugar, white birch sawdust is employed in an amount of 20% in the present invention.

③ Wheat Bran

Wheat bran contains proteins in an amount of 13.5%, crude fat in an amount of 3.8%, crude fiber in an amount of 10.4%, available carbohydrates in an amount of 55.40%, ash in an amount of 4.8%, and water in an amount of 12.1%. In addition, wheat bran has a vitamin BI content of 7.9 mg/kg, and contains 16 amino acids with a glutamic acid content amounting to 46%.

(2) Component Ratio in Medium

Oak sawdust, white birch sawdust and wheat bran were mixed at a ratio of 3:1:1 (v/v/v).

(3) Mixing

The dried raw materials are admixed together with water for about 2 hrs, with a water content of the mixture of within 60-62%. The resulting medium is preferably used within 4 hrs after its preparation.

2. Charging (Filling)

A culturing PP envelope with dimensions of height 60 cm×width 18 cm×thickness 0.055 mm is charged with the medium to a height of 42 cm, with the total weight amounting to 3.0 kg~3.2 kg. The upper part of the charged envelope is sealed using a capsule and then a cotton plug.

3. Sterilization

Sterilization was conducted at 105° C. for 70 min under atmospheric pressure, and then at 121° C. for 110 min (effective sterilization time) under a high pressure.

4. Cooling

The medium was cooled to 17° C. in a sterile cooling chamber kept at 7° C.

5. Inoculation

A void was formed in the medium by applying a perforator to the center of the medium. A seed strain was inoculated in an amount of 10 g per envelope to the void, followed by sealing with a cotton plug.

6. Cultivation

Individual envelopes were mounted on culture benches and incubated at 22° C. for 50 days under an air ventilator operating well. The atmosphere was maintained at a humidity of 60% with a carbon dioxide content of 1,200 ppm or less. A dark condition was maintained for the growth of the strain.

7. Browning

After transfer to a browning chamber, the envelope was perforated once or more times to adjust the water content. Browning was continued for 60 days. The number of perforations may be dependent on the water content so that the weight may be reduced to about 30% of that of the charged medium. Typically, the first perforation is conducted around 10 days after transfer to the browning chamber, and another perforation may be performed depending on the water content.

8. Breeding Management

After 60 days of browning, the media were moved to a breeding chamber and subjected to an immersion process. Preferably, the water for the immersion process is adjusted to a temperature of about 10° C. lower than room temperature before immersing the media in the water for 8 hrs. In addition, the water preferably has pH of 6.5. After completion of the water immersion, the media were placed on a desk to allow the mushrooms to bloom. The breeding chamber was maintained at an optimum temperature of 17~23° C. in a daylight condition and 5~10° C. in a nighttime condition, with humidity of 85%~90% in an early stage of mushroom blooming and 60% in a harvest stage. Generally, a crop may be obtained 15 days after the water immersion.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A shiitake strain *Lentinula edodes* (Berk.) Pegler GNA01 (accession No: KCCM11135P).

2. A mushroom produced from shiitake strain *Lentinula edodes* (Berk.) Pegler GNA01 (accession No: KCCM11135P).

3. The mushroom of claim 2, wherein the fruit body is spherical in shape with neither pilei nor stipes differentiating.

4. The mushroom of claim 2, wherein the fruit body exhibits a white blooming appearance on its surface.

5. The mushroom of claim 2, wherein the fruit body is asporogenous.

6. The mushroom of claim 5, wherein the fruit body is propagated by tissue dissociation of a part thereof.

7. A mushroom culture of the shiitake strain *Lentinula edodes* (Berk.) Pegler GNA01 (accession No: KCCM11135P) of claim 1.

8. An inoculum comprising the mushroom culture of claim 1.

* * * * *